United States Patent
Jang et al.

[11] Patent Number: 5,935,114
[45] Date of Patent: Aug. 10, 1999

[54] RAPID EXCHANGE DELIVERY CATHETER

[75] Inventors: Yue-Teh Jang, Fremont; Richard S. Ginn, San Jose; Stephen M. Salmon, Sunnyvale, all of Calif.

[73] Assignee: Cardiovascular Imaging Systems Incorporated, Sunnyvale, Calif.

[21] Appl. No.: 08/762,468

[22] Filed: Dec. 9, 1996

Related U.S. Application Data

[62] Division of application No. 08/271,878, Jul. 7, 1994, Pat. No. 5,620,417.

[51] Int. Cl.$^6$ .................................................. A61M 5/00
[52] U.S. Cl. ................................................. 604/264
[58] Field of Search .................... 604/165, 164, 604/52, 53, 96, 158, 108, 194; 128/656–658, 772

[56] References Cited

U.S. PATENT DOCUMENTS

| | | | |
|---|---|---|---|
| 4,411,655 | 10/1983 | Schreck | 604/165 |
| 4,451,256 | 5/1984 | Weiki et al. | 604/164 |
| 4,748,982 | 6/1988 | Horzewski et al. | 128/344 |
| 4,762,129 | 8/1988 | Bonzel | 128/344 |
| 4,817,613 | 4/1989 | Haraczewski et al. | 128/658 |
| 4,824,435 | 4/1989 | Giesy et al. | 604/49 |
| 4,850,358 | 7/1989 | Millar | 128/637 |
| 4,921,479 | 5/1990 | Grayzel . | |
| 4,932,413 | 6/1990 | Shockey et al. | 128/657 |
| 5,024,234 | 6/1991 | Leary et al. | 128/663.01 |
| 5,087,247 | 2/1992 | Horn et al. | 604/98 |
| 5,158,548 | 10/1992 | Lau et al. . | |
| 5,163,921 | 11/1992 | Feiring | 604/247 |
| 5,201,316 | 4/1993 | Pomeranz et al. | 128/662.06 |
| 5,203,338 | 4/1993 | Jang | 128/662.06 |
| 5,219,335 | 6/1993 | Willard et al. | 604/164 |
| 5,224,953 | 7/1993 | Morgentaler . | |
| 5,234,437 | 8/1993 | Sepetka . | |
| 5,257,974 | 11/1993 | Cox . | |
| 5,290,247 | 3/1994 | Crittenden . | |
| 5,306,244 | 4/1994 | Shiber . | |
| 5,383,889 | 1/1995 | Warner et al. . | |
| 5,385,562 | 1/1995 | Adams et al. . | |
| 5,620,417 | 4/1997 | Jang et al. | 604/96 |

*Primary Examiner*—John D. Yasko
*Assistant Examiner*—Manuel Mendez
*Attorney, Agent, or Firm*—Townsend and Townsend and Crew

[57] ABSTRACT

A catheter exchange member is provided for reducing exchange time when replacing one catheter (or similar device) with another in the vascular anatomy of a patient. The catheter exchange member includes a tubular body having a proximal and a distal end and a central lumen. A tapered fixture having a distal port and a proximal opening which is larger than the distal port is attached to the tubular body at the distal port. An elongate shaft is attached to and extends proximally from either the tapered fixture or the tubular body. The exchange member is preferably used within a conventional guiding catheter where the tubular body is advanced through a distal end of the guiding catheter and into the coronary artery while the tapered fixture remains in the guiding catheter. This configuration allows various therapeutic and diagnostic devices to be stored within the guiding catheter just proximal to the tapered fixture. One of the devices can be placed within the coronary artery by simply advancing it through the tapered fixture which channels the device into the tubular body and into the coronary artery. The device may be replaced with another by simply removing it and advancing the second device into the tapered fixture and into the coronary artery

10 Claims, 10 Drawing Sheets

RAPID EXCHANGE DELIVERY CATHETER

This is a division of application No. 08/271,878 filed Jul. 7, 1994, now U.S. Pat. No. 5,620,417, the disclosure of which is incorporated by reference.

BACKGROUND OF THE INVENTION

1. Field of the Invention

The present invention relates to the field of transluminal catheter procedures and interventions. In particular, the present invention provides a device and method for facilitating the rapid exchange of various therapeutic and diagnostic devices into the coronary arteries.

Percutaneous transluminal treatment of coronary artery disease frequently requires performance of multiple diagnostic and/or interventional procedures, each of which requires introduction of a different catheter. For example, intravascular ultrasound is often performed first and requires introducing a catheter having an imaging transducer into the heart. Following diagnosis, various therapeutic devices can be introduced into the heart, such as balloon angioplasty catheters, atherectomy catheters, laser ablation catheters, drug delivery catheters, and the like.

Before most therapeutic and diagnostic devices are introduced into a patient's vascular anatomy, a guiding catheter is first introduced into the heart as described generally in U.S. Pat. No. 5,163,921, the disclosure of which is herein incorporated by reference. The guiding catheter is typically inserted into the femoral artery in the groin and advanced towards the heart. The guiding catheter is directed through the patient's aorta until the distal tip of the guiding catheter reaches the ostium of one of the coronary arteries. Once the guiding catheter is placed in the ostium, various therapeutic or diagnostic devices can be inserted through the guiding catheter and into the coronary artery.

In order to introduce these devices beyond the distal end of the guiding catheter, a guide wire is commonly introduced through the guiding catheter. The distal end of the guide wire is advanced past the distal end of the guiding catheter and into the coronary artery. With the guide wire in place, a diagnostic or therapeutic catheter can be advanced over the guide wire and into the area of interest. The diagnostic or therapeutic catheter includes a lumen for receiving the guide wire, and the catheter is advanced over the guide wire in a manner often referred to as "tracking".

Frequently, it is necessary to exchange one therapeutic or diagnostic catheter for another. For instance, after initial diagnosis, it is usually necessary to remove the diagnostic catheter and replace it with an interventional catheter. Moreover, catheters having different sized balloons are often exchanged in an angioplasty procedure where lesions of the same vessel often require treatment with different size balloons. Following initial intervention, it is often desirable to reintroduce the diagnostic catheter to assess the progress that has been made. At the end of the treatment, it may be desirable to introduce a drug delivery catheter to perfuse the lesion with agents to inhibit restenosis. The exchange of catheters along a guide wire are described in U.S. Pat. Nos. 4,748,982; 4,762,129; 4,824,435; 4,850,358; and 5,024,234, the disclosures of which are hereby herein incorporated by reference.

In a particular procedure for exchanging catheters, the guide wire is left in place to protect the artery during the exchange. The guide wire is left in the artery because of complications that can arise when removing the guide wire, e.g., when the distal tip of the guide wire lifts a lesion flap, when the vessel spasms or abruptly closes making wire advancement impossible, or when placement of the guide wire simply takes too much time. To avoid these complications, the wire in this procedure is typically maintained in the vessel while the catheter exchange takes place.

Two techniques are generally employed for exchanging catheters when the guide wire is maintained in the artery. The first technique is used with catheters in which the guide wire lumen extends the full length of the catheter shaft. These are often referred to as "over-the-wire" catheters. When the "over-the-wire" catheter is withdrawn from the patient, guide wire position is maintained by holding the guide wire at its proximal end. To maintain a grip on the guide wire until the entire catheter is withdrawn from the patient, the guide wire must be long enough so that the proximal end of the guide wire can be held in place until the distal end of the catheter exits the patient. After the distal end of the catheter has been withdrawn from the patient, the grip at the proximal end of the guide wire may be withdrawn and the guide wire can be firmly held distal to the distal end of the catheter. The catheter can then be completely removed from the patient. The same procedure is performed in reverse to insert a different catheter into the patient.

In order to simplify catheter exchange, the second technique was developed which uses a "rapid exchange" catheter design. In the "rapid exchange" catheter, the guide wire lumen does not extend the full length of the catheter shaft. Instead, the guide wire exits the catheter shaft at some point near the distal end of the catheter. The remaining length of the guide wire runs alongside the catheter shaft until both the catheter and the guide wire exit the patient. This reduces the necessary length of the guide wire in comparison to the length required by the "over-the-wire" catheters.

One problem with existing intravascular systems arises from the need to position therapeutic or diagnostic devices into the narrow arteries of the heart The need to place the device over a guide wire requires that the distal end of the device be enlarged to accommodate the wire. The enlarged distal end can prevent the device from entering smaller arteries within the coronary vasculature. To overcome this problem, "common lumen" catheters have been developed as described in U.S. Pat. No. 5,203,338, the disclosure of which is hereby incorporated herein by reference. Common lumen catheters have a distal end having a single or common lumen and a proximal portion having at least two lumens, where one of the proximal lumens serves as a guide wire lumen. The common lumen catheter is inserted over a guide wire which has previously been inserted into the patient. After the common lumen catheter has been positioned at the desired location in the artery, the guide wire can be retracted from the distal region of the common lumen catheter and into one of the proximal lumens. This leaves the common lumen positioned in the distal region and available to receive the therapeutic or diagnostic device.

Despite improvements rendered by these techniques, certain difficulties still remain in performing coronary artery procedures. For instance, common lumen catheters occupy a substantial volume of the guiding catheter making it difficult to introduce contrast media through the guiding catheter. Additionally, even though the proximal portion of the common lumen is relatively large, space for housing the therapeutic or diagnostic devices is still limited. Because fewer devices can be stored in the common lumen catheter, the process of catheter exchange is slowed.

For these reasons it would be desirable to provide improved catheters and methods which overcome or reduce these and other problems.

2. Description of Background Art

Guiding catheters are described in U.S. Pat. Nos. 5,163, 921 and 4,817,613.

As previously described, "rapid exchange" type catheters are described in U.S. Pat. Nos. 4,748,982; 4,762,129; 4,824, 435; 4,850,358; 5,024,234.

As previously described, "common lumen" catheters are described in U.S. Pat. No. 5,203,338.

Other catheters employing guide wires are described in U.S. Pat. Nos. 5,201,316; 5,087,247; and 4,932,413, the disclosures of which are hereby herein incorporated by reference.

SUMMARY OF THE INVENTION

The present invention provides apparatus and methods for facilitating the rapid exchange of a variety of devices including therapeutic catheters, diagnostic catheters, and guide wires into the coronary arteries of the heart. The apparatus has a very small diameter proximal portion to reduce the occupied volume of the guiding catheter. Moreover, the invention increases the number of devices that can be positioned near the arteries by utilizing the entire interior portion of a conventional guiding catheter to hold the devices. By increasing the number of devices that can be held near the desired arteries, the time required to exchange these devices can be significantly decreased.

To provide these advantages, a catheter exchange member is positioned within a lumen of the guiding catheter near its distal end. The catheter exchange member includes a tubular body with proximal and distal ends and a central lumen. A tapered fixture having a distal port is attached to the proximal end of the tubular body so that the distal port is aligned with the central lumen. The tapered fixture further includes a proximal opening which is larger than the distal port. An elongate shaft is attached to and extends proximately from either the tapered fixture or the tubular body. In an exemplary aspect, the tubular body has a length in the range from 5 cm to 35 cm and inner diameter in the range from 0.5 mm to 1.5 mm. In another aspect, the proximal opening of the tapered fixture is radially expandable to a diameter in the range from 1.5 mm to 2.5 mm. In a further aspect, the proximal opening has a fixed diameter in the range from 1.2 mm to 2.0 mm.

In one particular aspect, the elongate shaft is a tubular member having a central lumen. Attached near the distal end of the tubular body and in fluid communication with the tubular member is an expandable balloon. Such a configuration allows the catheter exchange member to function as a balloon catheter. By having the catheter exchange member also function as a balloon catheter, additional space within the guiding catheter can be provided to store other therapeutic or diagnostic devices.

In another aspect, the tubular member has an infusion port. Through this port, drugs or other fluids can be delivered to the patient through the tubular member.

In one alternative embodiment of the catheter exchange member, the tapered fixture is a helical coil. In an alternative embodiment, the tapered fixture is a folded cone. In a further alternative embodiment, the tapered fixture includes a plurality of axial spring members supporting a flexible membrane.

In an alternative embodiment of the device of the present invention, a catheter exchange member for use in combination with a guiding catheter having an access lumen therethrough is provided. The catheter exchange member includes a tubular body having a proximal and a distal end and a central lumen. Means are provided at the proximal end of the tubular body for guiding a distally advancing catheter into the central lumen of the tubular body. Means are also provided for positioning the tubular body within the guiding catheter.

In a preferred aspect, the guiding means includes a tapered fixture having a distal end attached to the tubular body, a proximal opening having a diameter in the range from 1.2 mm to 2.0 mm, and a guide barrier between the distal end and proximal opening. Exemplary embodiments of the tapered fixture include a helical coil, a folded cone, or a plurality of axial spring member supporting a flexible membrane. In a further aspect, the positioning means includes an elongate shaft attached to and extending proximally from the guiding means.

In another aspect, the elongate shaft is a tubular member having a central lumen. Attached near the distal end of the tubular body and in fluid communication with the tubular member is an expandable balloon. Such a configuration allows the catheter exchange member to function as a balloon catheter. In a further aspect, the tubular member has an infusion port. Through this port, drugs or other fluids can be delivered to the patient through the tubular member.

The invention further provides a method for introducing an interactive element at the distal end of a catheter into a coronary artery. According to the method, a guiding catheter is introduced into the vasculature of a patient so that a distal end of the guiding catheter is at a coronary ostium. A tubular body is positioned within a lumen of the guiding catheter so that a proximal end of the tubular body is disposed within the guiding catheter and a distal end of the tubular body lies near a target location in the coronary artery. The distal end of the interactive catheter is then advanced through the lumen of the guiding catheter and into an open proximal end of the tubular body. The interactive catheter is then advanced through the lumen of the tubular body to the target location in the coronary artery.

In one particular aspect, the tubular body is positioned by axially translating an elongate shaft attached to the tubular body through the lumen of the guiding catheter.

In another aspect of the method, the proximal end of the tubular body includes a tapered fixture which acts as a guide to facilitate entry of the distal end of the interactive catheter into the lumen of the guiding catheter as the interactive catheter is advanced. In a further aspect, the tapered fixture includes a radially expandable proximal end for receiving the distal end of the interactive catheter. In yet another aspect, the interactive catheter is advanced into the tubular body without a movable guide wire.

In an exemplary aspect of the method, a guide wire is introduced through the guiding catheter into the coronary artery, and the tubular body is positioned over the guide wire. After the tubular body is at the desired location, the guide wire is withdrawn from the tubular body prior to advancing the distal end of the interactive catheter.

In yet another aspect, the distal end of the interactive catheter is withdrawn-from the tubular body. The distal end of a second catheter having an interactive device at its distal end is then advanced into the open proximal end of the tubular body to the target location in the coronary body.

In still another aspect, the tubular body is retracted relative to the guiding catheter to expose the interactive device within the target region of the coronary region. The tubular body can be retracted by withdrawing an elongate shaft attached to the tubular body through the lumen of the guiding catheter. In a preferred aspect, the interactive element is selected from the group consisting of ultrasonic transducers, angioplasty balloons, cutting blades, abrasive elements, fiber optic elements, and perfusion catheters.

In one particular aspect, a balloon near the distal end of the tubular body is expanded. Preferably, the balloon will be expanded in an area having a lesion. In a further aspect, a fluid is delivered through a tubular member that is attached to the tubular body. Preferably, the fluid will be a drug.

In yet another aspect of the method, the interactive catheter is a balloon catheter having a stent positioned around a balloon at a distal end of the balloon catheter. The balloon catheter is advanced through the tubular body until the stent is positioned at the target location. Once the stent is at the target location, the catheter exchange member is retracted until the stent is beyond the distal end of the tubular body. The balloon is then expanded to position the stent in the artery. The catheter exchange member can then be advanced until the tubular body is within the expanded stent.

In a further method a stent attached to a distal end of an interactive catheter is introduced into a coronary artery. According to the method, a guiding catheter is introduced into the vasculature of a patient so that a distal end of the guiding catheter is at a coronary ostium. The stent is then positioned snugly within a tubular body near a distal end of the tubular body. The tubular body having the stent is then inserted within a lumen of the guiding catheter so that a proximal end of the tubular body is disposed within the guiding catheter and the distal end of the tubular body lies near a target location in the coronary artery. The distal end of the interactive catheter having the stent is then advanced beyond the distal end of the tubular body to place the stent at the target location in the coronary artery.

In one particular aspect of the method, the interactive catheter is a balloon catheter having a balloon at its distal end. The stent is crimped to the balloon before placement of the balloon catheter into the tubular body so that both the stent and the tubular body can be advanced together through the guiding catheter. Once the stent is beyond the distal end of the guiding catheter; the balloon is expanded to position the stent within the target location.

In another aspect, the stent is self-expanding so that the stent can self-expand into the target area upon exiting the tubular body.

DESCRIPTION OF THE SPECIFIC EMBODIMENTS

Figure 1:
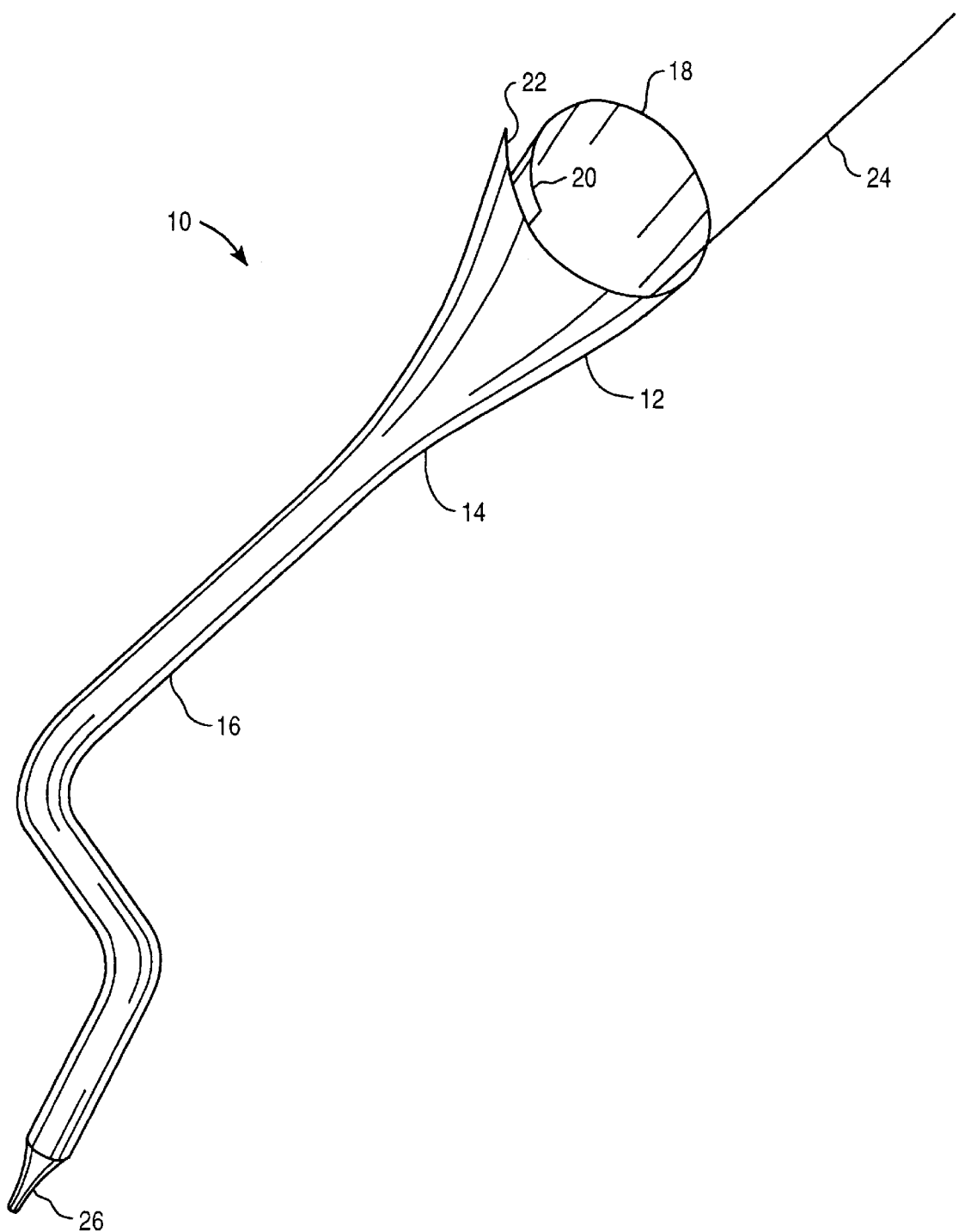
FIG. 1 illustrates a catheter exchange member having a folded cone for a tapered fixture according to the present invention.

The present invention provides a device and method for introducing and facilitating the rapid exchange of therapeutic, diagnostic, and other apparatus into the coronary arteries. The device comprises a catheter exchange member which is used within an access lumen of another catheter a guiding catheter introduced to the coronary arteries. The catheter exchange member includes a tubular body having a proximal and a distal end and a central lumen. Attached at the proximal end of the tubular body is a tapered fixture having a distal port and a proximal opening which is larger than the distal port. The distal port of the tapered fixture is aligned with the central lumen, and an elongate shaft is attached to and extends proximally from either the tapered fixture or the tubular body.

As described hereinafter, the tubular body serves as a path for a variety of therapeutic or diagnostic devices to a target location in the coronary artery. The therapeutic or diagnostic devices are advanced through a distal end of the tubular body and into the target location in the artery. In a preferred aspect, the tubular body has a length in the range from 5 cm to 35 cm and an inner diameter in the range from 1.2 mm to 2.0 mm. Exemplary materials for constructing the tubular body include polyethylene, polyurethane, silicone, and the like.

The tapered fixture serves as an anchor to maintain the catheter exchange member at a desired location in the guiding catheter and as a guide for delivering catheters from the guiding catheter into the tubular body. Preferably, the tapered fixture anchors the catheter exchange member near the distal end of the guiding catheter allowing the tubular body to pass through the distal end of the guiding catheter and into the coronary artery. The tapered fixture can be constructed in a variety of ways, an important feature being that it is able to maintain the catheter exchange member at the desired location in the guiding catheter. As described in detail hereinafter, the tapered fixture can be a helical coil, a folded cone, a plurality of axial spring member supporting a flexible membrane, or the like. These embodiments provide the necessary anchoring to hold the catheter exchange member in place. Preferably, the proximal opening of the tapered fixture will be radially expandable to a diameter in the range from 1.5 mm to 2.5 mm. This allows the tapered fixture to be adjustable fit within guiding catheters having differing or variable inner diameters. Alternatively, the proximal opening of the tapered fixture can have a fixed diameter in the range from 1.2 mm to 2.0 mm.

The tapered fixture is preferably configured so that contrast media, such as an angiographic die, can pass through the catheter exchange member and into the coronary arteries. The contrast media is used to enhance fluoroscopic imaging of the proper target location in the artery. To allow passage of the contrast media, the tapered fixture will preferably have a perforate structure, for example being provided with holes, slits, openings, or the like.

The tapered fixture also serves to direct catheters, guide wires, or similar devices into the tubular body when distally advanced through the guiding catheter towards the coronary artery. When a distal tip of one of these devices is advanced through the guiding catheter, it will engage the walls of the tapered fixture and be directed into the tubular body. Hence, a variety of these devices can be held within the guiding catheter just proximal to the catheter exchange member, the limiting factor being the inner diameter of the guiding catheter and the size of the devices. When one of the devices is needed at the target location in the artery, it is simply advanced from the guiding catheter into the tubular body and into the coronary artery. If the device is to be exchanged for another, it is simply retracted until its distal end is withdrawn from the catheter exchange member back into the guiding catheter. Another device can then advanced through the tapered fixture and into the tubular body.

By having the tapered fixture anchor the catheter exchange member to the guiding catheter and by having the tapered fixture direct interactive devices into the coronary artery, the guiding catheter itself can be used to store a variety of catheters having an assortment of interactive devices. The assortment of interactive elements can be those that are selected from the group consisting of ultrasonic transducers, angioplasty balloons, cutting blades, abrasive elements, and fiber optic elements. These interactive elements can be used for either therapeutic or diagnostic procedures. By utilizing the entire space of the access lumen of the guiding catheter (less the small area required by the elongate shaft), the number of these devices that can be stored is increased. Further, by storing these devices within the guiding catheter itself, the devices can more rapidly be exchanged with each other when a different device is required within the coronary artery.

The elongate shaft is used to advance the catheter exchange member into and along the guiding catheter. Hence, the elongate shaft should have sufficient rigidity and column strength to be able to advance the catheter exchange member through the guiding catheter lumen. In an exemplary embodiment, the elongate shaft is a flexible rod or "hypotube". The rod or "hypotube" is typically constructed from stainless steel or other medically acceptable metals. Alternatively, the elongate shaft can be a tubular member with a central lumen for delivering fluid to a location near the distal end of the tubular body. The fluid delivered can be used to inflate a balloon near the distal end of the tubular body, or can be a drug that is delivered to the patient through a port in the tubular member.

Referring to FIG. 1, an exemplary embodiment of a catheter exchange member 10 having a cone shaped tapered fixture 12 is shown. Attached to a distal port 14 of the tapered fixture 12 is a tubular body 16. The tapered fixture 12 further includes a proximal opening 18 which is larger in diameter than the distal port 14.

The tapered fixture 12 has a slot along its length resulting in two overlapping ends which form a folded cone. This configuration allows the proximal opening 18 to be radially expandable to a diameter necessary to engage the walls of the guiding catheter and to provide an anchor. Alternatively, the proximal opening 18 can be configured so that its diameter is fixed, i.e. by not slitting the tapered fixture. By fixing the diameter, the catheter exchange member 10 can be advanced through a guiding catheter having a decreasing inner diameter at its distal end so that its proximal opening 18 engages the guiding catheter near its distal end.

The tapered fixture 12 is preferably constructed of the same material used to construct the tubular body. Alternatively, the tapered fixture 12 can be constructed of polyethylene, polyurethane, silicone, and the like. The use of these materials allow for advantages such as strength, biocompatibility, low friction, low cost, and ease of manufacture.

Attached anywhere along the tapered fixture 12 or the tubular body 16 is a flexible rod 24. As previously described, the rod is used to advance the exchange member 10 through a guiding catheter towards the coronary artery.

The tubular body 16 is flexible so that it can be advanced into the distal regions of the coronary arteries while also having sufficient strength to advance the catheter exchange member along the guiding catheter. Optionally, the tubular body can have a distal tip 26 through which a guide wire or interactive device can be advanced into the coronary artery. Optionally the flexible rod 24 could also be attached to the distal tip 26.

In an exemplary use, the catheter exchange member 10 is inserted into a guiding catheter beginning with the distal tip 26. The flexible rod 24 is then used to advance the exchange member 10 through the guiding catheter toward the coronary artery. The distal tip 26 and a distal portion of the tubular body 16 are advanced through a distal end of the guiding catheter and into the desired regions of the coronary artery. The tapered fixture 12 engages the walls of the guiding catheter and anchors the exchange member 10 within a distal portion of the guiding catheter. Since the tapered fixture 12 is radially expandable, the exchange member 10 can be configured to engage the guiding catheter at any desired location. Once properly anchored, therapeutic or diagnostic devices can be advanced into the guiding catheter and up to the proximal opening 18. When one of these devices is selected to be advanced into the desired location in the coronary artery, the device can simply be advanced into the tapered fixture 12 which will direct the device into the tubular body 16, out the distal tip 26, and into the desired location.

Figure 1A:
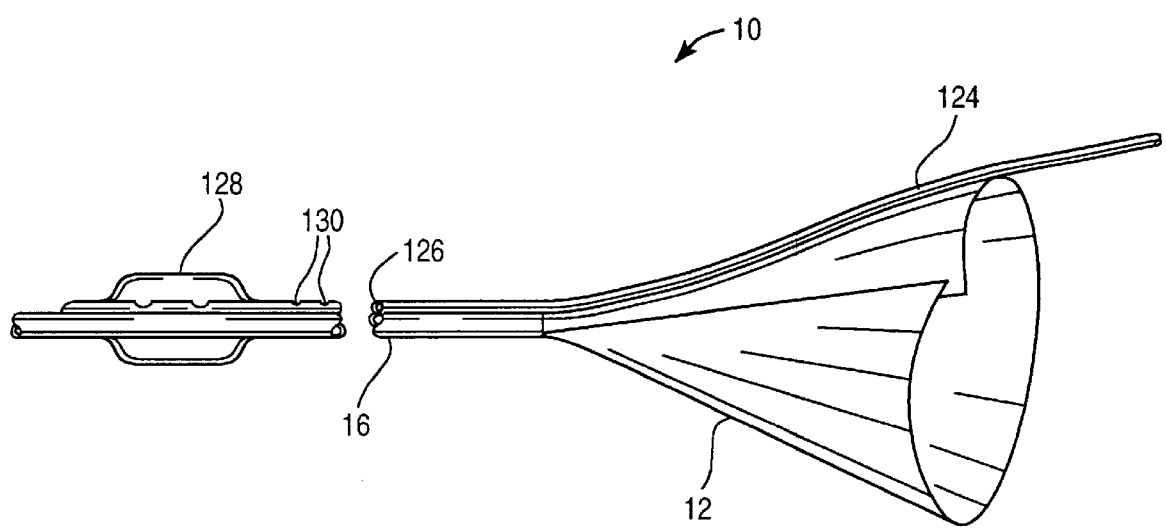
FIG. 1A illustrates an alternative embodiment of the catheter exchange member of FIG. 1 having a tubular member as a positioning shaft.

The catheter exchange member 10 can be provided with a tubular member 124 in place of the flexible rod 24 as shown in FIG. 1A. Tubular member 124 can be attached anywhere along the tapered fixture 12 or the tubular body 16. Tubular member 124 includes a central lumen 126 for delivering a fluid. The fluid can be used to inflate an expandable balloon 128 near the distal end of the tubular body 16. Preferably, the balloon 128 will be an angioplasty balloon. In this manner, the tubular body 16 and the balloon 128 can function as an angioplasty balloon catheter in addition to functioning as an exchange member. Such a configuration eliminates the need to store this type of balloon catheter in the guiding catheter, thereby providing additional space in the guiding catheter which can be used to store other therapeutic or diagnostic devices.

The tubular member 124 can also be provided with a plurality of infusion ports 130. By providing ports 130, the tubular member 124 can be used as an infusion tube for administering drugs or other fluids to the patient.

Tubular member 124 is preferably constructed of a stiff plastic or metal tube so that the tubular member has sufficient stiffness to push and direct the catheter exchange member 10 into the coronary artery. Although shown with the embodiment of FIG. 1, the tubular member 124 can equally be included in the embodiments shown in FIGS. 2 and 3 which are described hereinafter.

Figure 2:
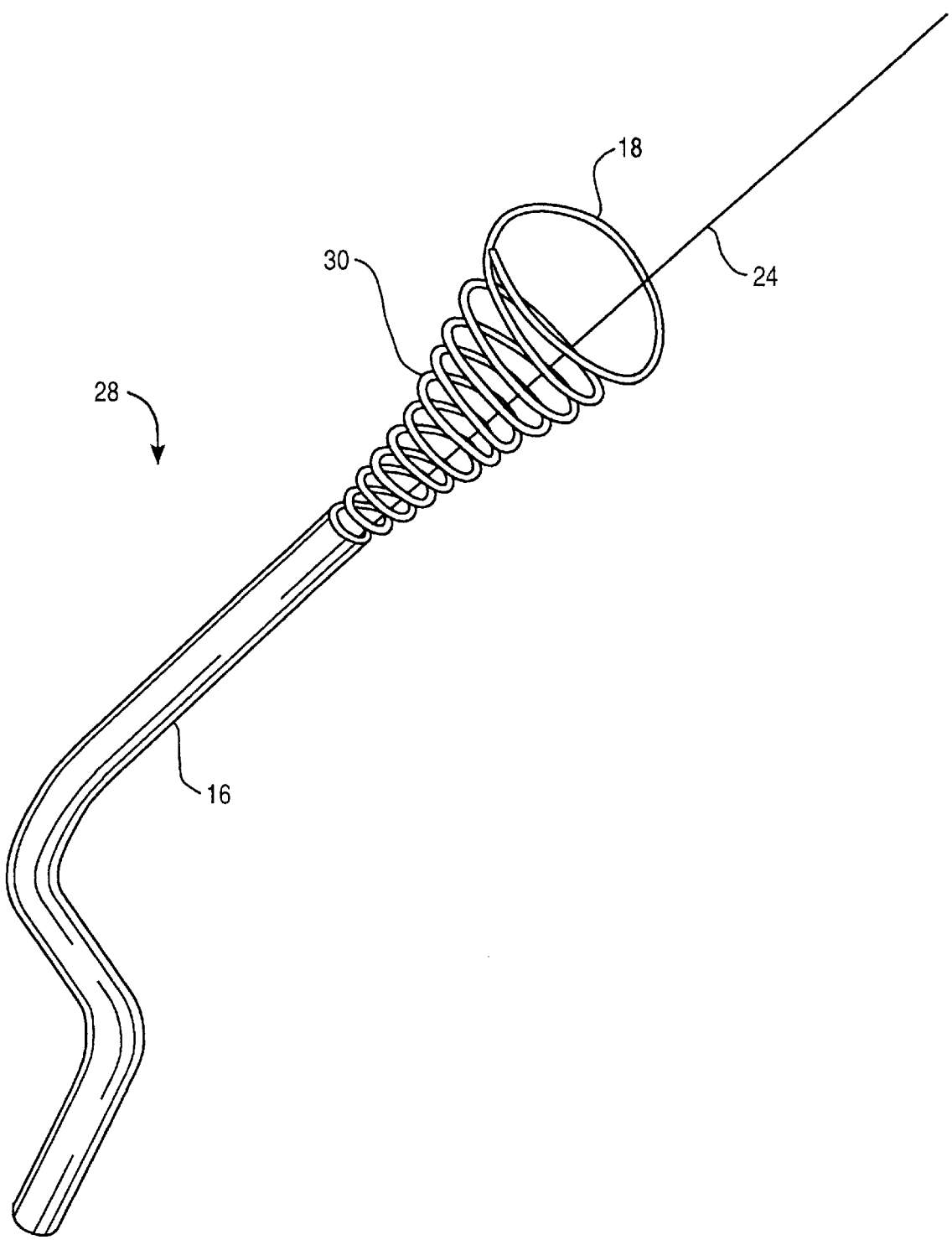
FIG. 2 illustrates a catheter exchange member having a helical coil for a tapered fixture according to the present invention.

An alternative embodiment of a catheter exchange member is shown in FIG. 2 and is designated by reference numeral 28. The catheter exchange member 28 is essentially identical to the catheter exchange member 10 of FIG. 1 except for the tapered fixture. For convenience of discussion, all of the elements of the catheter exchange member 28 will use identical reference numerals as illustrated in FIG. 1 except for the tapered fixture. The catheter exchange member 28 of FIG. 2 includes a helical coil tapered fixture 30 and is constructed from a tapered spring coil. A distal end of the coil is attached to a proximal end of the tubular body 16. The proximal opening 18 of the tapered fixture 30 contacts the lumen walls of the guiding catheter and serves to funnel devices that are advanced through the guiding catheter and into the tubular body 16.

One advantage of using a tapered spring coil is that it allows contrast media to be delivered into the artery for angiographic assessment. The layers of the coils are spaced sufficiently apart for delivery of the contrast media, and are also sufficiently close together to prevent guide wires from slipping through the tapered fixture 30 when distally advanced. The gap between the layers of the coil will preferably be in the range from 0.10 mm to 0.25 mm, and more preferably at about 0.20 mm. A preferable material for the helical coil is stainless steel, nitinol, nylon, and the like. The flexible rod 24 can be attached anywhere along the tapered fixture 30 or alternatively anywhere along the tubular body 16. Preferably, the rod 24 will be attached to the proximal coil layers.

Figure 3:
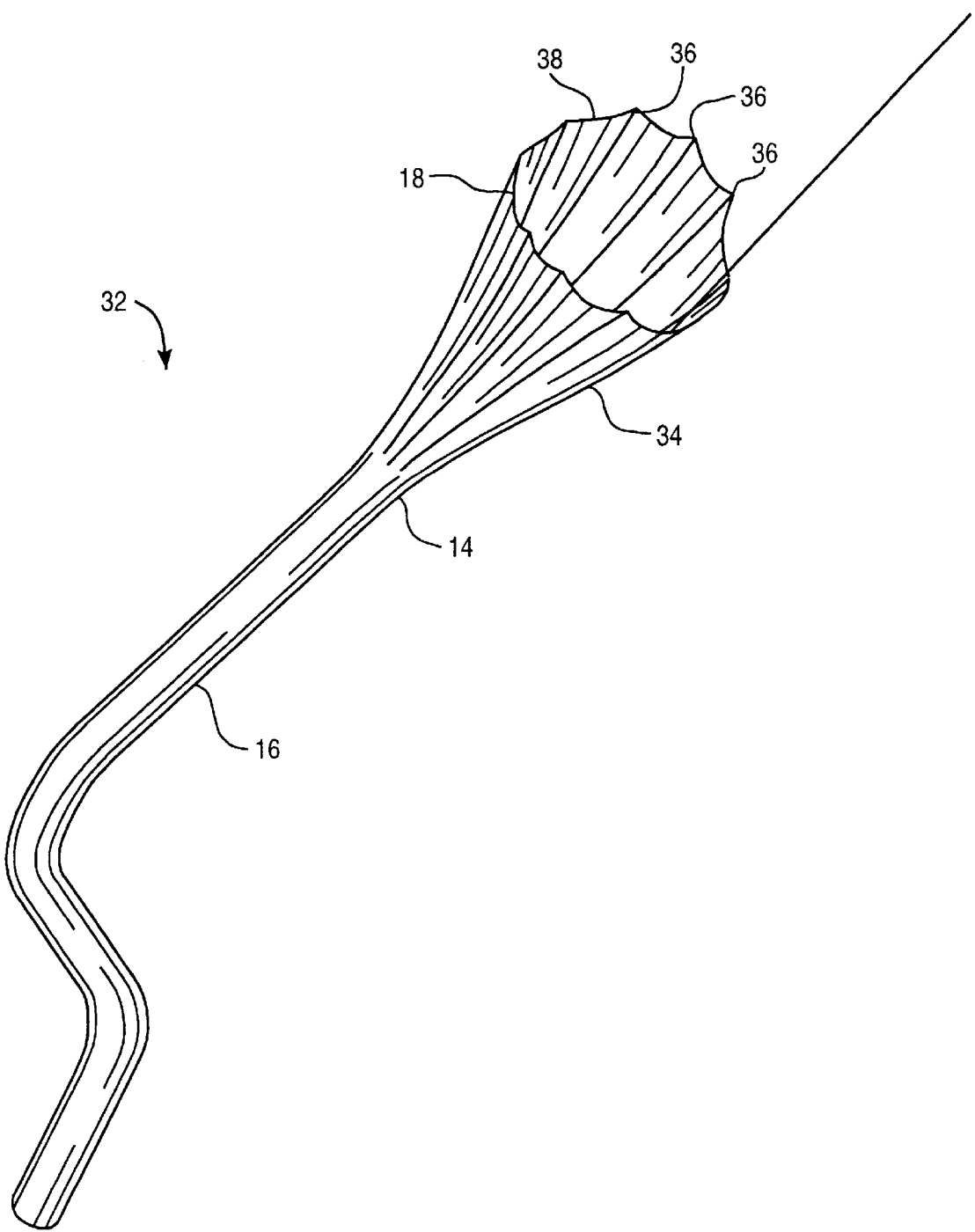
FIG. 3 illustrates a catheter exchange member having a plurality of axial spring members supporting a flexible membrane for a tapered fixture according to the present invention.

Yet another embodiment of a catheter exchange member 32 is shown in FIG. 3. The catheter exchange member 32 contains elements essentially identical to the catheter exchange member of FIG. 1 except for the tapered fixture. The catheter exchange member 32 employs a "umbrella type" tapered fixture 34. The tapered fixture 34 has a plurality of axial spring members 36 that support a flexible membrane 38. The axial spring members 36 are outwardly biased in a radial direction causing the proximal opening 18 to be larger than the distal port 14. The tapered fixture 34 functions similar to a conventional spring loaded umbrella. The spring members 36 serve to engage the inner walls of the guiding catheter to provide an anchor. The spring members along with the flexible membrane 38 also serve to channel or funnel any devices inserted through the guiding catheter and into the tubular body 16. The flexible membrane 38 is preferably constructed of polyethylene, polyurethane, silicone, and the like and allows fluids, such as contrast media, to flow to the coronary arteries. The tapered fixture 34 can be used with different sizes of guiding catheters because of the radially expandable axial spring members 36 which engage the inner walls of the guiding catheter.

Figure 4:
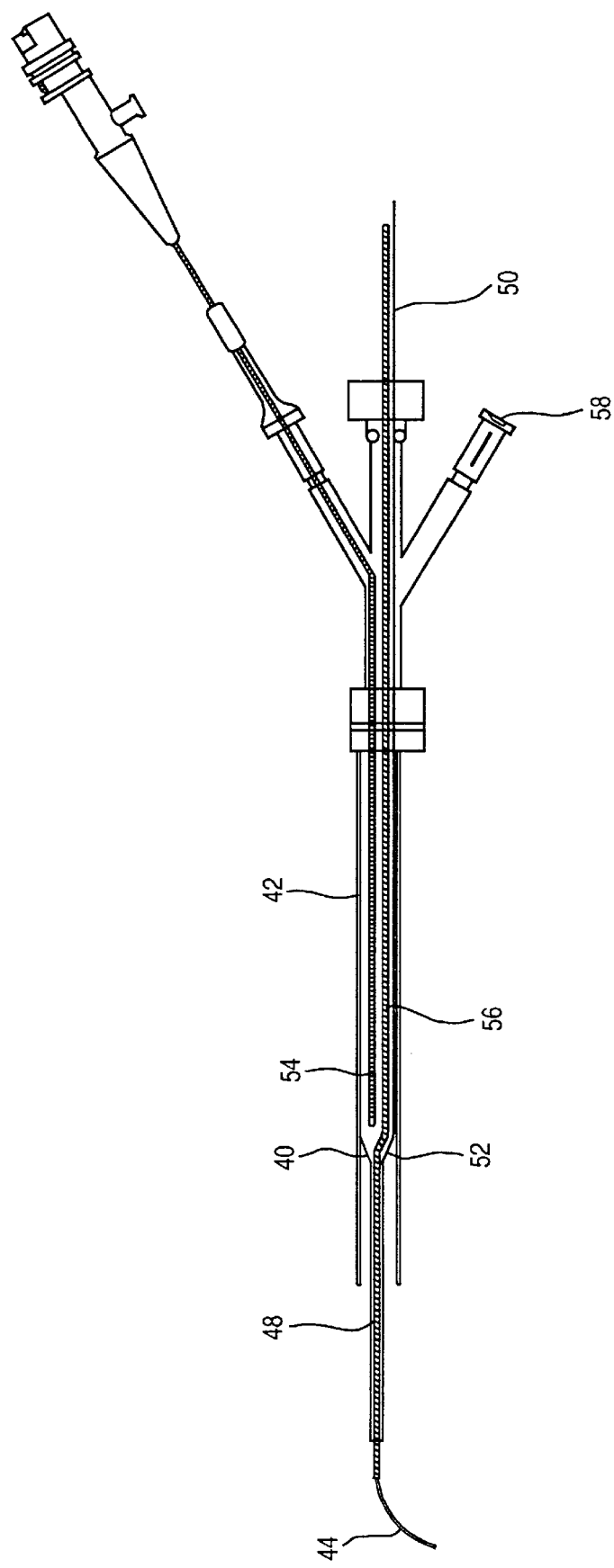
FIG. 4 illustrates a catheter exchange member disposed within a lumen of a guiding and having therapeutic and diagnostic devices located therein according to the present invention.

Referring to FIG. 4, an exemplary embodiment of catheter exchange member 40 in combination with a guiding catheter 42 will be described. The guiding catheter 42 is initially placed in the coronary ostium and a guide wire 44 is advanced through the guiding catheter 42 and into a distal portion of the coronary artery. The catheter exchange member 40 is then advanced over a proximal end of the guide wire 44 and into the guiding catheter 42. The exchange member 40 can be advanced over the entire length of the guide wire 44. Alternatively, the guide wire 44 can be advanced only through a distal portion of the tubular body 48 so that only a certain percentage of the tubular body 48 will track over the guide wire 44 and into the coronary artery.

To advance the exchange member 40 through the guiding catheter 42 and into the coronary artery, a flexible rod 50 attached to a tapered fixture 52 (or to the tubular body 48) of the catheter exchange member 40 is axially advanced to direct the exchange member 40 along the guide wire 44. The exchange member 40 is advanced through the guiding catheter 42 until it reaches a distal portion of the guiding catheter 42. The tubular body 48 is then advanced through a proximal end of the guiding catheter 42 and into a distal portion of the coronary artery while the tapered fixture 52 remains anchored in the guiding catheter 42.

Once the tubular body 48 is at the desired location, the guide wire 44 can be withdrawn into the guiding catheter 42. Diagnostic and therapeutic devices, such as an ultrasound imaging core 54 or a balloon catheter 56 can be advanced into the guiding catheter 42 and up to the catheter exchange member 40. Alternatively, the guide wire 44 can be left in the artery and the balloon catheter 56 advanced over the guide wire 42 as shown in FIG. 4.

The number of devices that can be stored in the guiding catheter 42 depends both upon the size of the guiding catheter 42 and the size of the devices. To insert one of these devices into the coronary artery, it is simply advanced through a proximal opening in the tapered fixture 52 which directs the device into the tubular body 48 where it can be further advanced into the artery. If another device is needed within the artery, the first device can be removed by pulling it from the tubular body 48 and advancing the second device into the tapered fixture 52 where the second device will be directed into the tubular body 48 and into the coronary artery.

As previously described, when positioning a device such as a balloon catheter 56 within the tubular body 48, it is often necessary to inject contrast media through the tapered fixture 52 so that the location of the balloon can fluoroscopically be determined. The guiding catheter 42 includes a port 58 for injecting the contrast media into the guiding catheter. The tapered fixture 52 is configured so that the contrast media can pass therethrough and allow for fluoroscopic positioning of the balloon catheter 56.

Figure 5:
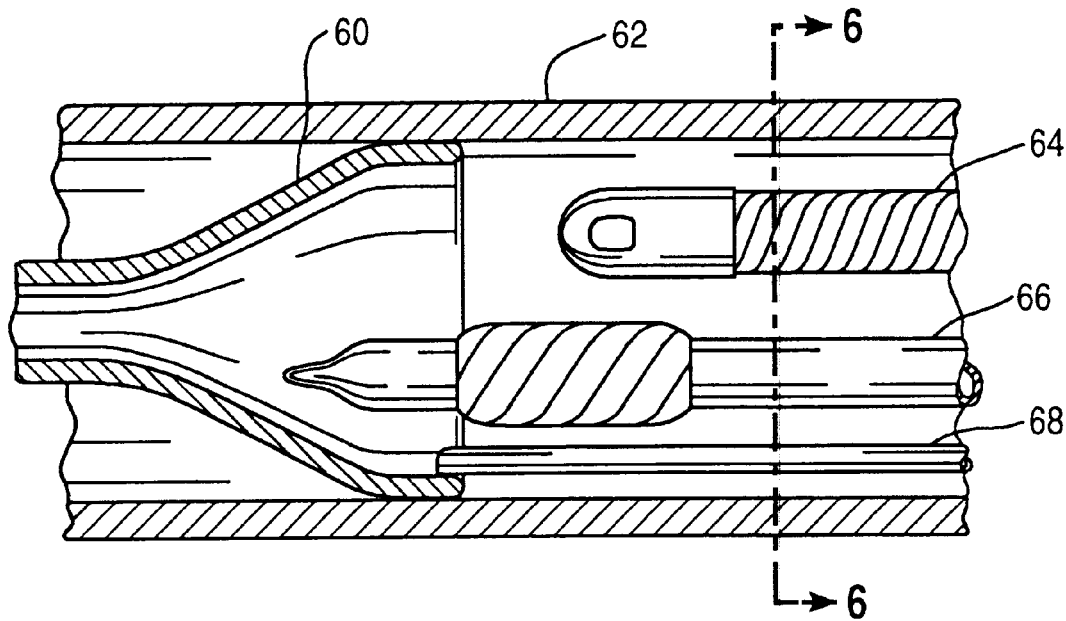
FIG. 5 is a cross-section view showing a catheter exchange member disposed with a guiding catheter and having therapeutic and diagnostic devices located therein according to the present invention.
Figure 6:
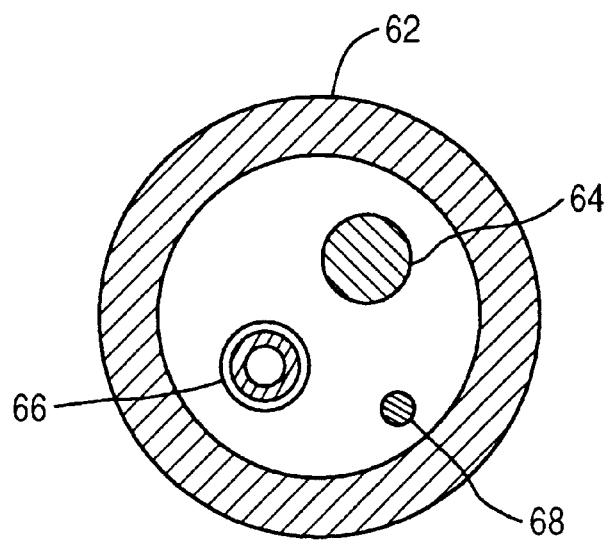
FIG. 6 is a view of the guiding catheter of FIG. 5 taken along line 6—6.

Referring to FIGS. 5 and 6, an enlarged view of a catheter exchange member 60 is shown to illustrate the positioning of various diagnostic or therapeutic devices when stored within a guiding catheter 62. The guiding catheter 62 will have a central lumen with an inner diameter in the range from about 1.5 mm to 2.5 mm. The catheter exchange member will be small enough to enable it to be advanced through the central lumen. When the catheter exchange member 60 is placed within the guiding catheter 62, the entire area of the central lumen proximal to the catheter exchange member 60 can be used to store various therapeutic and diagnostic devices such as an ultrasound imaging transducer 64 and a balloon catheter 66.

The balloon catheter 66 will typically have a diameter in the range from 0.5 mm to 1.0 mm, and the imaging transducer 64 will typically have a diameter in the range from 0.3 mm to 1.0 mm. Also stored within the lumen of the guiding catheter 62 is a flexible rod 68 that is used to advance the exchange member 60 as previously described. This will typically have a diameter in the range from about 0.1 mm to 0.25 mm. The central lumen of the guiding catheter 62 is large enough to accommodate a plurality of devices having diameters in the ranges as just described, thereby allowing for a number of devices to be rapidly exchanged and positioned into the coronary artery.

Figure 7:
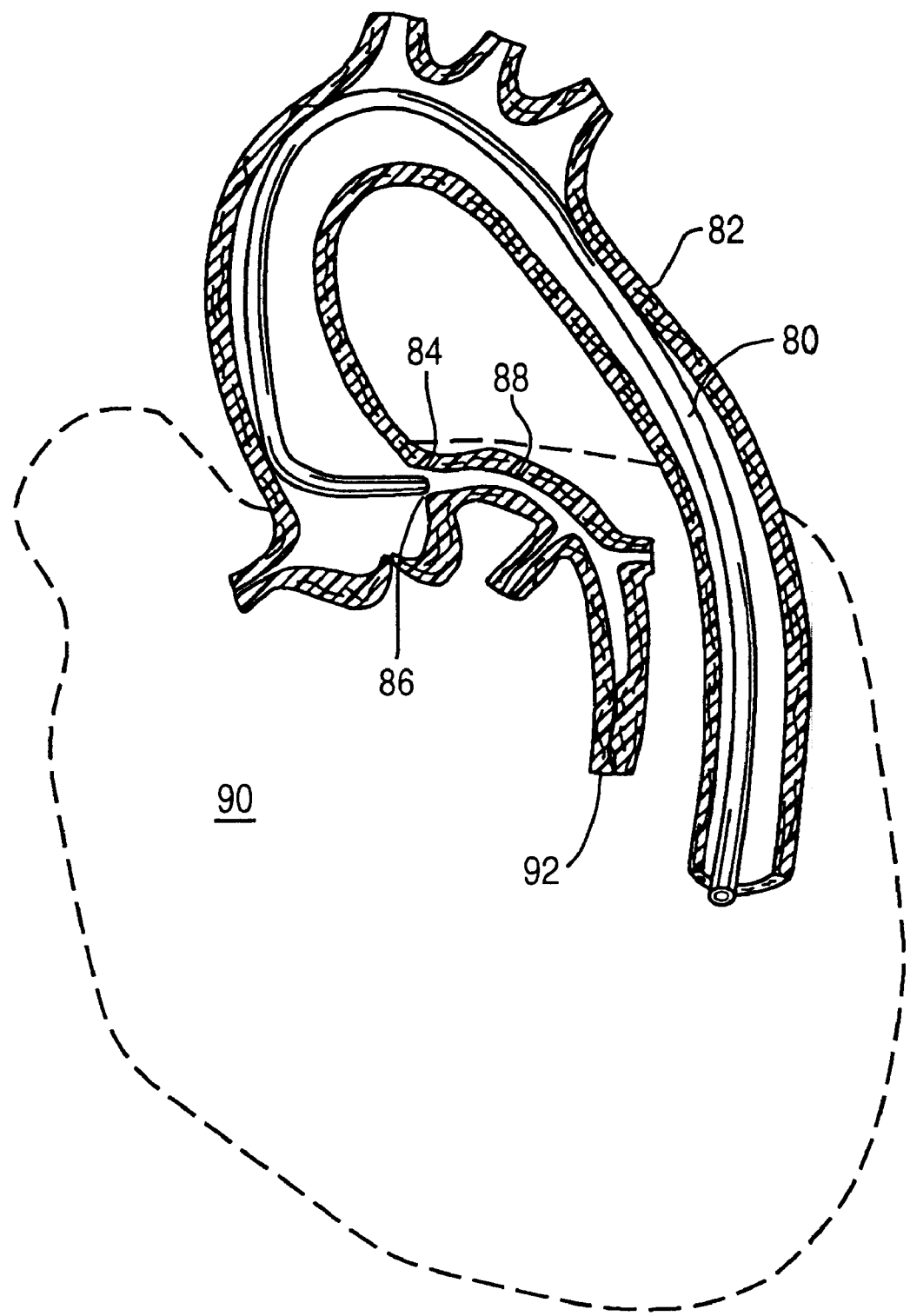
FIGS. 7–9 illustrate an exemplary method for inserting a guiding catheter into a coronary ostium and using a catheter exchange member to facilitate the placement of therapeutic and diagnostic devices into the coronary arteries.
Figure 8:
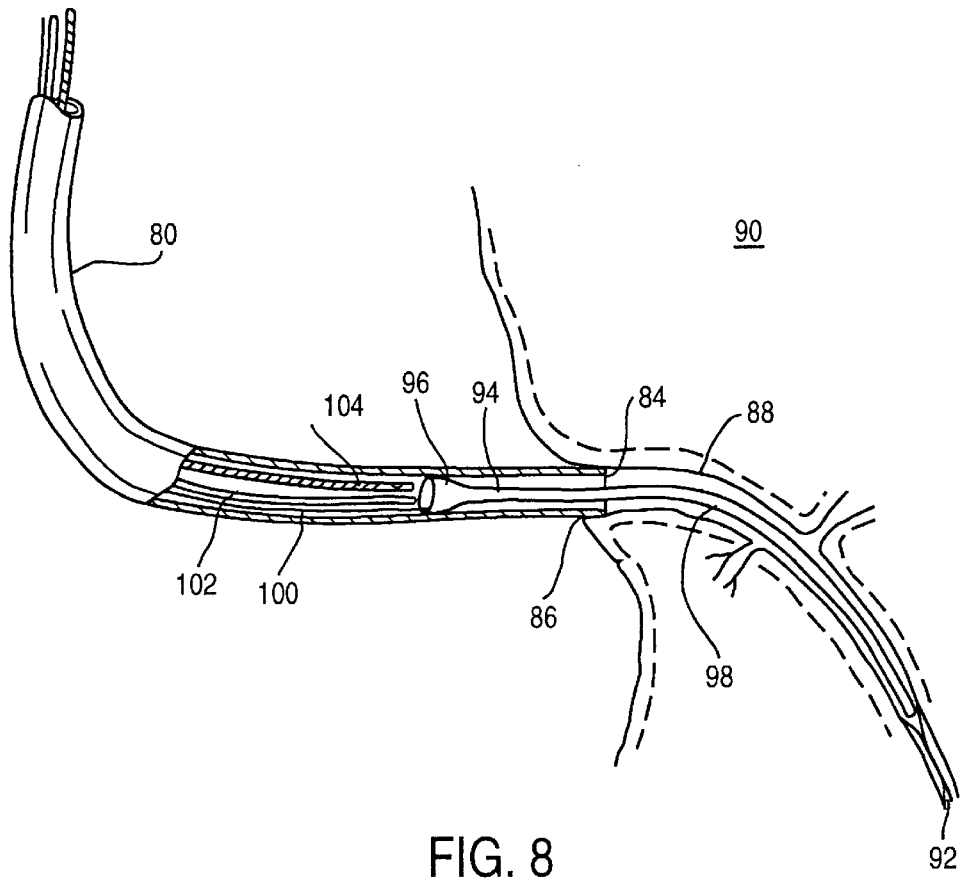
Figure 9:
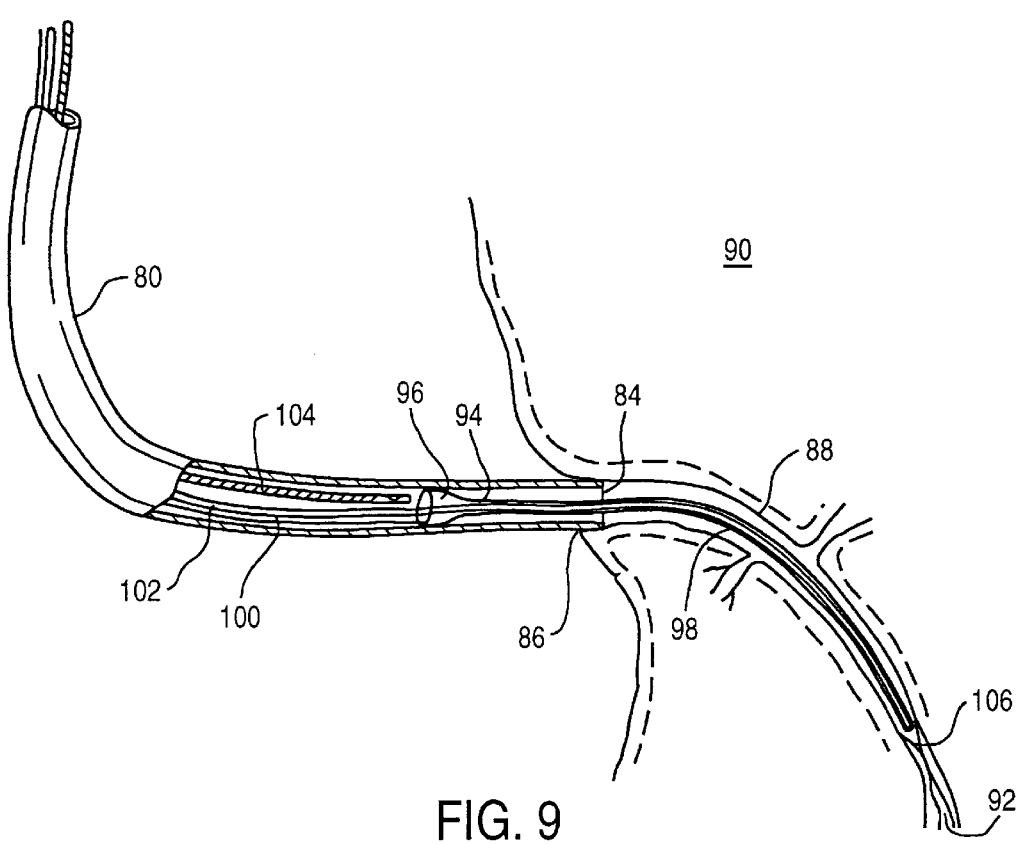

An exemplary method of using a catheter exchange member to facilitate the exchange of therapeutic and diagnostic devices in the coronary arteries is shown in FIGS. 7–9. A guiding catheter 80 is initially directed through the aorta 82 until a distal tip 84 reaches the coronary ostium 86 of the main coronary artery 88. The coronary artery 88 delivers oxygenated blood to the myocardium 90. Along a branch of the coronary artery 88 is a lesion 92 which restricts blood flow. The guiding catheter 80 serves as a guide for therapeutic or diagnostic devices that are directed to the lesion 92.

As shown in FIG. 8, a catheter exchange member 94 is inserted through a proximal end of the guiding catheter 80 until a tapered member 96 of the catheter exchange member 94 is near the distal tip 84. At this point, a tubular body 98 of the catheter exchange member 94 will extend into the coronary artery 88 and near the lesion 92. A rod 100 is used to advance the catheter exchange member 94 through the guiding catheter 80. A variety of therapeutic or diagnostic devices, such as a balloon catheter 102 and a ultrasonic imaging transducer 104, can then be advanced into the guiding catheter 80 until just proximal to the catheter exchange member 94.

One of these devices can then be selected and advanced through the catheter exchange member 94 and into the coronary artery 88. As shown in FIG. 9, the balloon catheter 102 is advanced into the catheter exchange member 94 and is funneled into the tubular body 98 by the tapered member 96. A distal tip 106 of the balloon catheter 102 is advanced beyond the tubular body 98 until it reaches the lesion 92. The balloon catheter 102 is then ready to assist in the desired therapy. After therapy, the balloon catheter 102 can be withdrawn from the catheter exchange member 94 and another device inserted in its place.

The catheter exchange member 94 can be used to facilitate a variety of other procedures within the coronary artery. For example, before therapy is performed, a diagnostic procedure may be required. In that event, the ultrasound imaging transducer 104 may first be placed near the lesion 92 by advancing it from the stored position just proximal to the catheter exchange member 94. After imaging the artery, the imaging transducer 104 is withdrawn from the tubular body 98 and stored in the guiding catheter 80 just proximal to the catheter exchange member 94.

As another example; the tubular body 98 can be advanced into the lesion 92 before a therapeutic or diagnostic device is advanced into the catheter exchange member 94. The therapeutic or diagnostic device, such as the balloon catheter 102, can be advanced into the tubular body 98 until reaching the lesion 92. The catheter exchange member 94 can then be withdrawn from the lesion 92 to expose the balloon to the artery. Balloon dilation may then occur. After treatment is completed, the exchange member 94 can be readvanced over the balloon catheter 102 until the distal end of the tubular body 98 is once again established in the desired location.

In a further example, a guide wire can be stored in the guiding catheter 80 and can be advanced from its stored position into the coronary artery at any time.

Figure 9A:
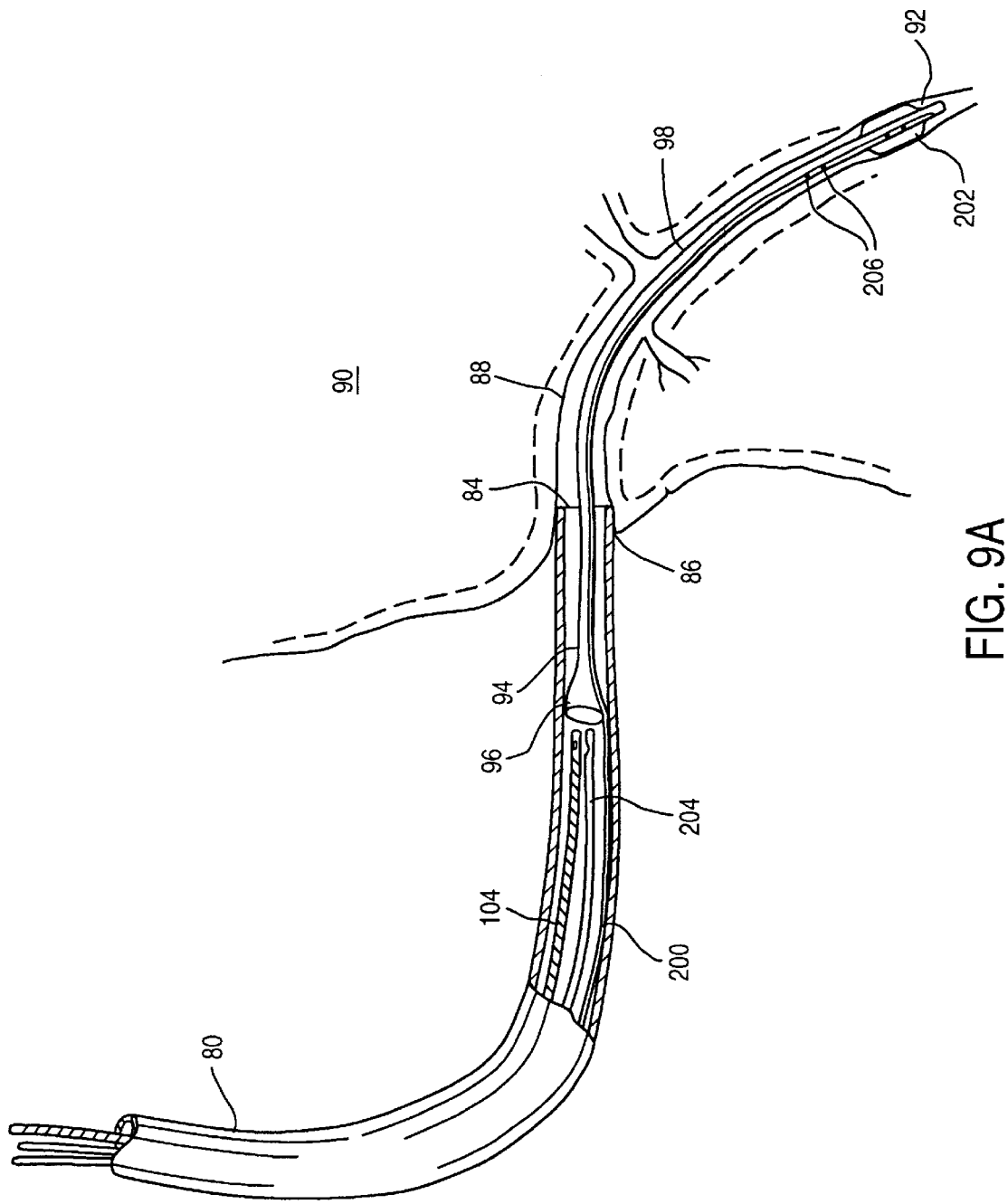
FIG. 9A illustrates an alternative use of the catheter exchange member of FIGS. 7–9 when provided with an expandable balloon.

In an alternative method, the catheter exchange member 94 can be provided with a tubular member 200 as shown in FIG. 9A. Tubular member 200 has a central lumen in fluid communication with a balloon 202 near the distal end of the tubular body 98. The inclusion of the balloon 202 allows the catheter exchange member 94 to function as a balloon catheter in addition to functioning as an exchange member. For instance, instead of advancing the balloon catheter 102 of FIG. 9 to the lesion 92, the tubular body 98 can be advanced until the balloon 202 is near the lesion 92. At this point, the balloon dilation can occur as shown in FIG. 9A. By having the catheter exchange member 94 also function as a balloon catheter, another therapeutic or diagnostic device (such as a cutting blade 204) can be substituted for the balloon catheter 102 of FIG. 9. The therapeutic or diagnostic devices stored in the guiding catheter can be advanced into the tubular body 98 as previously described.

Optionally, the tubular member 200 can be used to deliver drugs or other fluids to the patient by providing a plurality of infusion ports 206. Of course, the infusion ports 206 would be closed if balloon dilation were proscribed so that the balloon inflation fluid would reach the balloon 202. Once the catheter exchange member 94 is in the desired position, drug therapy can occur by injecting drugs through the tubular member 200 which will exit to the patient from the infusion ports 206. Preferably, the balloon 202 will not be included if infusion ports 206 are employed from drug delivery.

In a further use, the catheter exchange member can be used to assist in placing a conventional stent within the coronary artery. Conventional stents, such as those commercially available from Johnson & Johnson and Cook, are applied to an area of the artery having a lesion by a balloon catheter. The stent is typically crimped over a deflated balloon on the catheter. The balloon is used to expand the stent in the artery when inflated Alternatively, the stent can be self-expanding and need not be crimped over a balloon. Such stents will preferably be constructed of nitinol having shape memory.

Typically, a sheath is placed over the stent during insertion. The sheath is then retracted to expose the stent to the artery and the stent is deployed. The catheter exchange member of the present invention can be used as a sheath to protect the stent during insertion into the lesionous area. After the stent has been appropriately applied, the catheter exchange member can then be used as previously described to direct any one of a variety of therapeutic or diagnostic devices into an area within the expanded stent.

Figure 10:
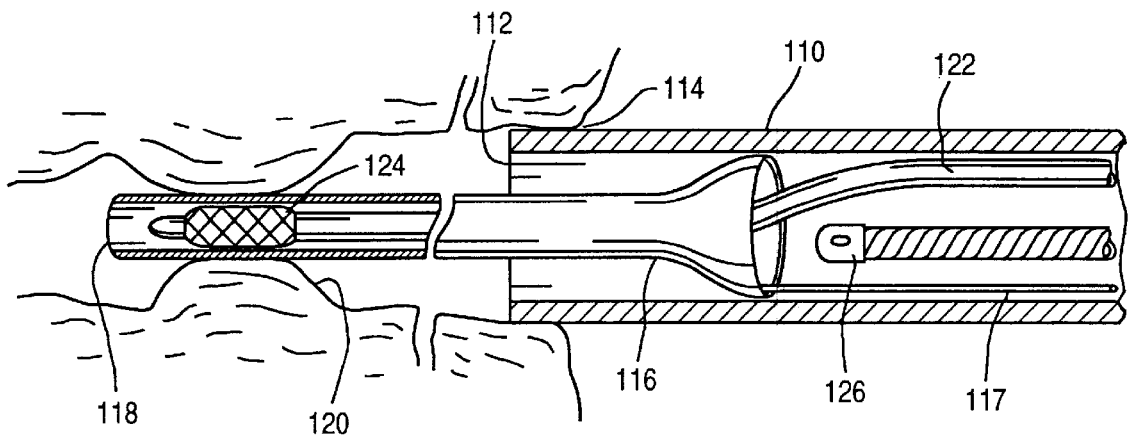
FIGS. 10–12 illustrate a method for utilizing a catheter exchange member to both facilitate the placement of a stent within the coronary arteries and to facilitate the exchange of therapeutic and diagnostic devices within the expanded stent according to the present invention.
Figure 11:
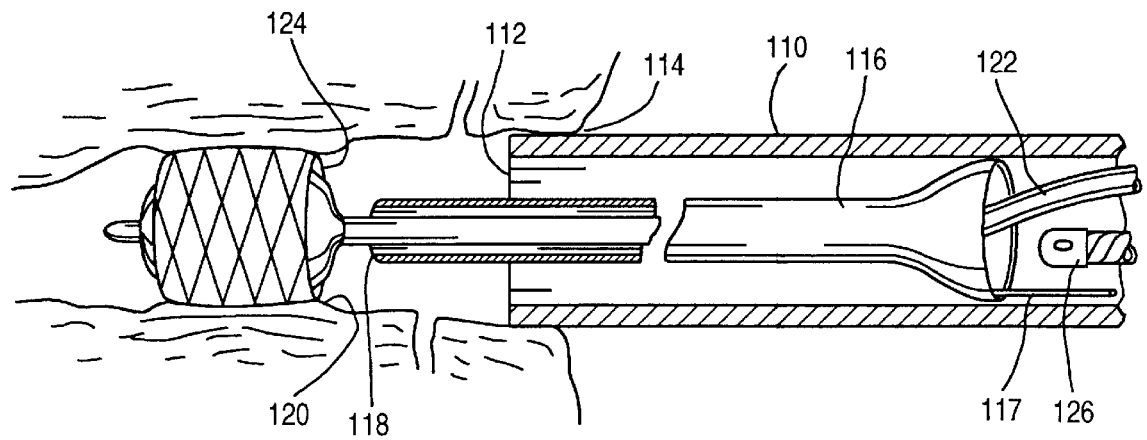
Figure 12:
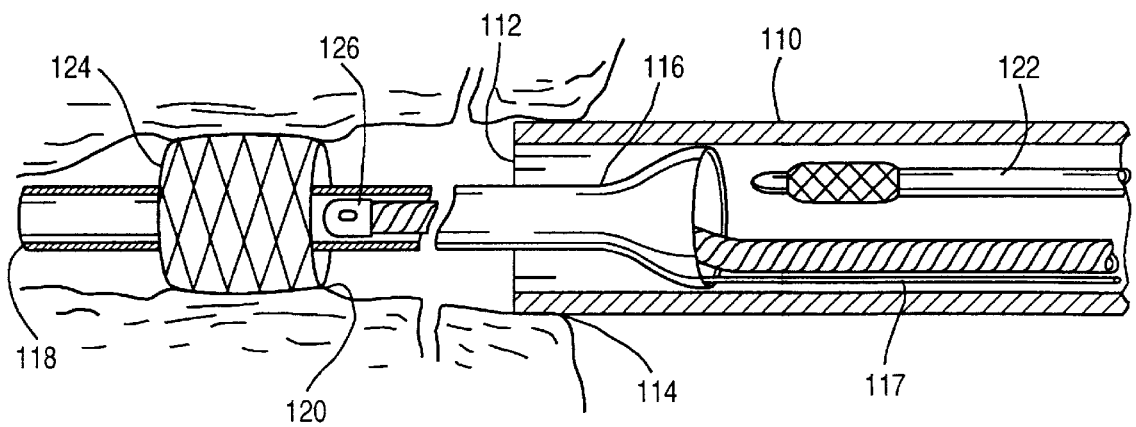

An exemplary use of a catheter exchange member to insert a stent is shown in FIGS. 10–12. Initially a guiding catheter 110 is inserted into the patient until a distal tip 112 reaches the coronary ostium 114 as previously described. A catheter exchange member 116 is then advanced by a shaft 117 along the guiding catheter 110 until a distal end 118 of the catheter exchange member 116 reaches a lesion 120 as shown in FIG. 10. A balloon catheter 122 having a stent 124 over a balloon and an ultrasonic imaging transducer 126 are then inserted into the guiding catheter 110 and advanced until just proximal to the catheter exchange member 116. The balloon catheter 122 is then advanced into the catheter exchange member 116 until the stent 124 reaches the lesion 120.

The catheter exchange member 116 is then withdrawn from the region having the lesion 120, and the balloon on the catheter 122 is inflated to expand the stent 124 as shown in FIG. 11. Once the stent 124 is expanded, the catheter exchange member 116 is again advanced so that the distal end 118 is within the expanded stent 124 as shown in FIG. 12. The ultrasound imaging transducer 126 is then inserted into the distal end 118 of the catheter exchange member 116 where the imaging transducer 126 can be used to help determine the location of the stent 124.

In an alternative method, the stent 124 can be placed within the catheter exchange member 116 near the distal end 118 before the catheter exchange member 116 is introduced into the guiding catheter 110. Preferably, the stent 124 will be snugly fit within the catheter exchange member 116. Both the catheter exchange member 116 and the balloon catheter 122 having the stent 124 are then advanced together through the guiding catheter. In this manner, the catheter exchange member 116 serves as a sheath to prevent inadvertent embolization of the stent 124 before reaching the target location. Once the catheter exchange member is inserted, the stent can be positioned at the target location as previously described.

Although the foregoing invention has been described in some detail by way of illustration and example, for purposes of clarity of understanding, it will be obvious that certain changes and modifications may be practiced within the scope of the appended claims.

What is claimed is:

1. A catheter exchange member comprising:

a tubular body having a proximal end, a distal end, and a central lumen;

a tapered fixture having a distal port connected to the tubular body and aligned with the central lumen and a proximal opening which is larger than the distal port, the tubular body and the tapered fixture forming a subassembly, and an elongate shaft having a proximal end and a distal end, wherein the distal end is fixedly attached to the subassembly and wherein the proximal end is disposed proximally from the subassembly.

2. A catheter exchange member as in claim 1, wherein the tubular body has a length in the range from 5 cm to 35 cm and an inner diameter in the range from 0.5 mm to 1.5 mm.

3. A catheter exchange member as in claim 1 wherein the proximal opening has a fixed diameter in the range from 1.2 mm to 2.0 mm.

4. A catheter exchange member as in claim 1, wherein the elongate shaft is a flexible rod.

5. A catheter exchange member for use in combination with a guiding catheter having an access lumen therethrough, said catheter exchange member comprising:

a tubular body having a proximal end, a distal end, and a central lumen;

means at the proximal end of the tubular body for guiding a distally advancing catheter into the central lumen of the tubular body, the guiding means comprising a tapered fixture having a distal end attached to the tubular body, a proximal opening having a diameter in the range from 1.2 mm to 2.5 mm; and an elongate shaft having a proximal end and a distal end, wherein the distal end is fixedly attached to the tubular body or the guiding means, and wherein the proximal end of the shaft is disposed proximally of the guiding means to position the tubular body within the guiding catheter.

6. A catheter exchange member as in claim 5, wherein the tubular body has a length in the range from 5 cm to 35 cm and an inner diameter in the range from 0.5 mm to 1.5 mm.

7. A catheter exchange member as in claim 5, wherein the guiding means further comprises a guide barrier between the distal end and proximal opening.

8. A catheter exchange member as in claim 7, wherein the proximal opening has a fixed diameter in the range from 1.2 mm to 2.0 mm.

9. A catheter exchange member as in claim 5, wherein the guiding means and the tubular body form a subassembly, and wherein the elongate shaft is attached to and extends proximally from the subassembly.

10. A catheter exchange member as in claim 9, wherein the elongate shaft is a flexible rod.

* * * * *